United States Patent [19]
Kometani et al.

[11] Patent Number: 5,945,533
[45] Date of Patent: *Aug. 31, 1999

[54] PROCESS FOR PREPARING OPTICALLY ACTIVE BENZOTHIAZEPINE COMPOUND AND INTERMEDIATE THEREFOR

[75] Inventors: Tadashi Kometani, Toyama; Hiroaki Matsumae; Takeji Shibatani, both of Kobe, all of Japan

[73] Assignee: Tanabe Seiyaku Co., Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/909,077

[22] Filed: Aug. 14, 1997

[30] Foreign Application Priority Data

Aug. 26, 1996 [JP] Japan .................................. 8-223523

[51] Int. Cl.$^6$ ................................................ C07D 281/02
[52] U.S. Cl. ............................................................ 540/491
[58] Field of Search ............................................. 540/491

[56] References Cited

U.S. PATENT DOCUMENTS

| | | |
|---|---|---|
| 5,102,999 | 4/1992 | Giordano et al. ................. 540/491 |

FOREIGN PATENT DOCUMENTS

| | | |
|---|---|---|
| 362556 | 4/1990 | European Pat. Off. . |
| 45-9383 | 4/1970 | Japan . |
| 60-25982 | 2/1985 | Japan . |
| 60-25983 | 2/1985 | Japan . |
| 486727 | 5/1992 | Japan . |
| 5-244992 | 9/1993 | Japan . |

OTHER PUBLICATIONS

Matsumae et al., "Microbial Asymmetric Reduction of (RS)–2–(4–Methoxyphenyl)–1,5–benzothiazepin–3, 4(2H, 5H)–dione, the Key Intermediate in the Synthesis of Diltiazem Hydrochloride", *Journal of Fermentation and Bioengineering*, vol. 79, No. 1, pp. 28–32, 1995.

Kometani et al., "Production of (2S,3S0–2, 3–Dihydro–3–hydroxy–2–(4–methoxyphenyl)–1, 5–benzothiazepin–4(5H)–one, a Key Intermediate for Diltiazem Synthesis," J. Fermentation and Bioengineering, vol. 84, No. 3, pp. 195–199, Mar. 1997.

*Primary Examiner*—Richard L. Raymond
*Assistant Examiner*—Ann Kessinger
*Attorney, Agent, or Firm*—Finnegan, Henderson, Farabow, Garrett & Dunner, L.L.P.

[57] ABSTRACT

Powdery aggregate of 2-phenyl-1,5-benzothiazepin-3,4(2H, 5H)-dione compound:

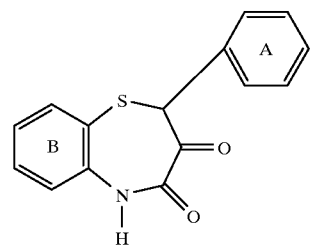

(II)

wherein Ring A and Ring B are benzene ring having optionally substituent selected from lower alkyl, lower alkoxy and halogen, which is prepared by admixing solution of the compound (II) in polar organic solvent with solvent which does not substantially dissolve the compound (II) but is miscible with said polar organic solvent, and separating and collecting the resultant particles of the compound (II). Said aggregate of the compound (II) can be converted into optically active 3-hydroxy-2-phenyl-2,3-dihydro-1,5-benzothiazepin-4(5H)-one compounds (I) on industrial scale, which are useful as intermediate for various medicaments.

9 Claims, 5 Drawing Sheets

PROCESS FOR PREPARING OPTICALLY ACTIVE BENZOTHIAZEPINE COMPOUND AND INTERMEDIATE THEREFOR

TECHNICAL FIELD

The present invention relates to a process for preparing an optically active benzothiazepine compound, or an intermediate therefor. More particularly, the present invention relates to a powdery aggregate of 2-phenyl-1,5-benzothiazepin-3,4(2H,5H)-dione compound having an improved solubility in water, and a process for preparing an optically active 3-hydroxy-2-phenyl-2,3-dihydro-1,5-benzothiazepin-4(5H)-one compound, which comprises subjecting the said aggregate to asymmetrically enzymatic reduction.

PRIOR ART

Optically active 3-hydroxy-2-phenyl-2,3-dihydro-1,5-benzothiazepin-4(5H)-one compound is a very important intermediate for preparing various medicaments, such as diltiazem hydrochloride (chemical name; (2S,3S)-3-acetoxy-5-[2-(dimethylamino)ethyl]-2,3-dihydro-2-(4-methoxyphenyl)-1,5-benzothiazepin-4(5H)-one hydrochloride) which is useful as a coronary vasodilator.

Hitherto, as a process for preparing an optically active 3-hydroxy-2-phenyl-2,3-dihydro-1,5-benzothiazepin-4 (5H)-one compound, there is a known process which comprises subjecting a racemic 3-phenylglycidic acid ester compound to asymmetric hydrolysis by treating it with an esterase or a lipase (cf., EP-A-362556), and reacting the resulting optically active 3-phenylglycidic acid ester compound with an aminothiophenol compound.

Further, JP-A-5-244992 and Journal of Fermentation & Bioengineering (Vol. 79, No. 1, pp. 28–32 (1995)) disclose a process for preparing an optically active 3-hydroxy-2-phenyl-2,3-dihydro-1,5-benzothiazepin-4(5H)-one compound which comprises subjecting a 2-phenyl-1,5-benzothiazepin-3,4(2H,5H)-dione compound to asymmetrically enzymatic reduction. However, these publications do not mention the use of an aggregate as a starting material. Moreover, EP-A-486727 discloses a process for preparing a stereospecific 3-hydroxy-4-phenyl-2,3-dihydro-1-benzazepin-2(2H)-one compound by treating a 4-phenyl-1-benzazepin-2,3-dione compound with a reductase or a reductase-producing microorganism. However, this publication never discloses detailed description as to methods of asymmetric reduction, nor discloses the use of an aggregate as a starting compound.

Among the known processes, according to the process of subjecting a racemic 3-phenylglycidic acid ester compound to asymmetric hydrolysis and then reacting an optically active 3-phenylglycidic acid ester compound with an aminothiophenol compound, the starting racemic 3-phenylglycidic acid ester cannot be fully utilized, at most 50% thereof, and in order to utilize 100% of the optically active 3-phenylglycidic acid ester compound, the process additionally requires complicated procedures such as recovery of an opposite (undesired) optically active isomer and re-raceminzation thereof.

Besides, in the known processes of enzymatically reducing a 2-phenyl-1,5-benzothiazepin-3,4(2H,5H)-dione compound to give a corresponding 3-hydroxy-4(5H)-one compound, the starting compound is added to an aqueous solvent for the enzymatic reaction in the form of crystal or in the form of a solution in a solubilizer such as dimethylformamide (DMF), etc. When the starting compounds are used in the form of crystal as a substrate for enzymatic reaction, they are hardly charged into the reaction system on a large scale, because the starting compounds are usually insoluble or hardly-soluble in water. And hence, the conversion from the starting compound into the desired compound cannot be achieved in a sufficient yield. On the other hand, when using a solubilizer such as an organic solvent (e.g., DMF, etc.), the substrate can be used in somewhat large amount. However, in this case, the solubilizer is also required to be used in an increased amount, and it causes production of by-products (e.g., S-oxide of the starting compound, etc.) or inhibition of the enzyme activity. Consequently, the reaction efficiency (e.g., yield of the desired product) is often reduced.

Under the above-mentioned circumstances, it is desired to develop an improved process for preparing an optically active benzothiazepine compound, which is suitable for industrial production thereof.

BRIEF DESCRIPTION OF INVENTION

An object of the present invention is to provide a powdery aggregate of 2-phenyl-1,5-benzothiazepin-3,4(2H,5H)-dione compounds.

Another object of the present invention is to provide a process for preparing optically active 3-hydroxy-2-phenyl-2,3-dihydro-1,5-benzothiazepin-4(5H)-one compound by using said powdery aggregate.

DETAILED DESCRIPTION OF INVENTION

The present inventors have intensively studied and have found that in a process for preparing an optically active 3-hydroxy-2-phenyl-2,3-dihydro-1,5-benzothiazepin-4 (5H)-one compound by asymmetrically enzymatic reduction, when using as a starting compound (substrate) a powdery aggregate of 2-phenyl-1,5-benzothiazepin-3,4(2H, 5H)-dione compound which is prepared by a specific method and has an improved solubility in water, a large amount of the substrate, e.g., 100 g/liter can be charged in one reaction vessel, by which the desired optically active compound, which is useful as an intermediate for medicaments, can be advantageously produced in a high yield on an industrial scale.

That is, according to the present invention, an optically active 3-hydroxy-2-phenyl-2,3-dihydro-1,5-benzothiazepin-4(5H)-one compound of the formula (I):

wherein Ring A and Ring B are a benzene ring which may optionally be substituted by a group selected from a lower alkyl group, a lower alkoxy group and a halogen atom, is prepared efficiently and on an industrially large scale, by the following steps:

(i) dissolving a 2-phenyl-1,5-benzothiazepin-3,4(2H,5H)-dione compound of the formula (II):

wherein Ring A and Ring B are the same as defined above, in a polar organic solvent (hereinafter, referred to as the primary solvent) which can dissolve the above compound (II), (ii) admixing the solution thus obtained with a solvent (hereinafter, referred to as the secondary solvent) which does not substantially dissolve the compound (II) but is miscible with the primary solvent, (iii) separating and collecting the resulting particles of the compound (II) to give a powdery aggregate of the compound (II) having an improved solubility in water, and then (iv) subjecting the product to asymmetrically enzymatic reduction, whereby one carbonyl group thereof being reduced to a hydroxymethylene group.

The primary solvent which can dissolve the compound (II) means a polar organic solvent which can dissolve the compound (II) at a concentration of more than 1 mg/ml at 30° C., and has a dielectric constant of more than 25. Among such polar organic solvents, a polar organic solvent which can dissolve the compound (II) at a concentration of more than 10 mg/ml at 30° C. is preferable. Examples of the polar organic solvent are N,N-dimethylformamide, dimethylsulfoxide, methanol, ethanol, acetonitrile, etc., and N,N-dimethylformamide, dimethylsulfoxide and methanol are more preferable.

The above-mentioned primary solvent can be used in an amount which is determined depending on the solubility of the compound (II) in the solvent, etc., but is preferably used in an amount sufficient to completely dissolve the predetermined amount of the compound (II). For example, the amount of the primary solvent varies depending on the properties of the polar organic solvent to be used or the properties of the compound (II), but the amount of the primary solvent is controlled so that the concentration of the compound (II) in the primary solvent is in the range of 1 to 400 mg/ml, especially in the range of 1 to 200 mg/ml.

The solvent which does not substantially dissolve the compound (II) and is miscible with the primary solvent includes, for example, a polar solvent such as water, and among the polar solvents, water is the most preferable because it can be easily and safely handled or from an economical view point.

The amount of the secondary solvent is not limited, but when the primary solvent is N,N-dimethylformamide, the secondary solvent is used in a volume of 2 to 1000 times, preferably in a volume of 10 to 50 times, of the volume of the primary solvent.

The addition and mixing of the solution of the compound (II) in the primary solvent into the secondary solvent is carried out, for example, by adding dropwise the compound (II) solution into the secondary solvent, if necessary, with stirring, at a temperature from 5 to 40° C., preferably at room temperature. When adding the compound (II) solution into a secondary solvent, the mixture immediately becomes emulsion-like, but, by allowing the mixture to stand or by stirring it for an appropriate period (e.g., 30 to 60 minutes), aggregation of the particles of the compound (II) proceeds, and the aggregate can be easily separated and collected in the form of powder.

The separation and collection of the powder (aggregate) of the compound (II) thus obtained is carried out by a conventional method such as centrifugation or filtration, and the collected powdery aggregate in a wet condition can be used in a subsequent asymmetrically enzymatic reduction, and the aggregate can be used in the reduction process if necessary, after washing and drying.

Figure 1:
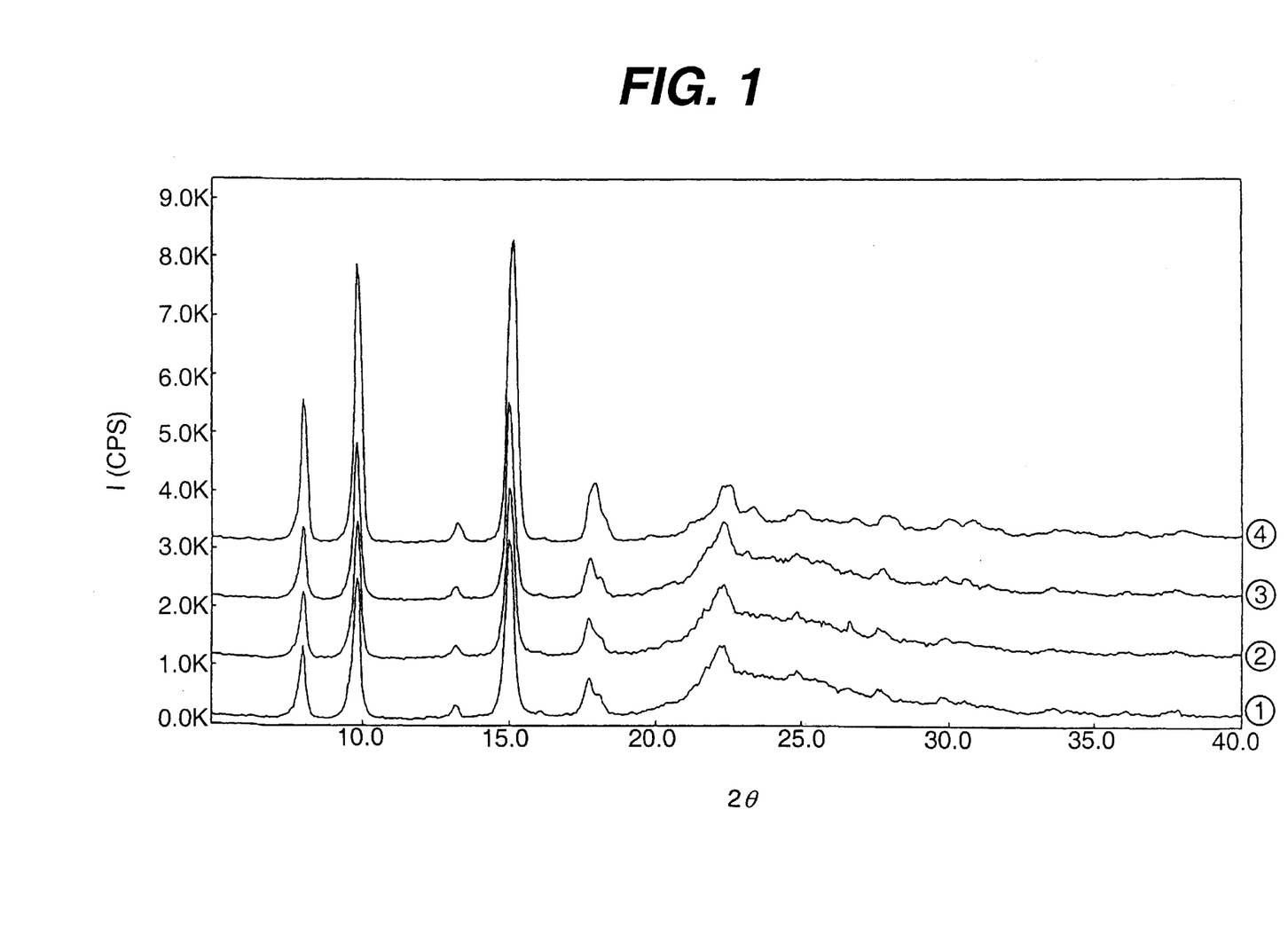
FIG. 1 shows the X-ray powder diffraction pattern of the powdery aggregate of 2-(4-methoxyphenyl)-1,5-benzothiazepin-3,4(2H,5H)-dione which is obtained in Examples 1 to 4.

The powdery aggregate of the compound (II) thus obtained shows a higher solubility in water by twice or more than the original crystals of the compound (II) does, for example, the solubility of the powdery aggregate of the compound (II) in water is more than 20 mg/liter at 30° C. The melting point of the powdery aggregate of the compound (II) slightly varies according to the properties of the primary solvent to be used, and it is in the range of 120° C. to 140° C., which is significantly lower than the melting point of the original crystals of the compound (II), i.e., 163° C. Besides, the powdery aggregate of the present invention has an X-ray powder diffraction pattern as follows:

a) a single and clear diffraction peak is at around $2\theta=8.0°$ ($8.0°\pm0.15°$), $2\theta=9.9°$ ($9.9°\pm0.15°$) and $2\theta=15.1°$ ($15.1°\pm0.15°$), respectively, b) the diffraction peak at around $2\theta=15.1°$ has the maximum relative X-ray intensity among all peaks, and c) when the relative intensity of the peak at around $2\theta=15.1°$ is adjusted to 1.00, that of the peaks at around $2\theta=8.0°$ and $2\theta=9.9°$ is in the range of about 0.30 to 0.50 and about 0.70 to 0.95, respectively and no peak other than those mentioned above has the relative X-ray intensity of more than 0.30 (see FIG. 1).

Meanwhile, from the results of X-ray powder diffractometry, it is assumed that the aggregate of the present invention is a mixture (composition) comprising crystalline form and amorphous form of the compound (II).

According to the study of the present inventors, an optically active 3-hydroxy-2-phenyl-2,3-dihydro-1,5-benzothiazepin-4(5H)-one compound (I) can be obtained at a good efficiency by asymmetrically enzymatic reduction of the above-mentioned powdery aggregate of the compound (II) having an improved solubility in water.

That is, by using the powdery aggregate having a high solubility in water, water can be used as a solvent in the asymmetrically enzymatic reduction. Besides, the concentration of a substrate can be increased without using a solubilizer, so that said asymmetric reduction is carried out at a high efficiency and on an industrial scale, to give the desired optically active benzothiazepine compound (I).

When Ring A and Ring B are a benzene ring having a substituent selected from a lower alkyl group, a lower alkoxy group and a halogen atom, the asymmetrically enzymatic reduction of the aggregate of the compound (II) is carried out in the same manner as when Ring A and Ring B are a benzene ring having no substituent. The substituent on Ring A includes, for example, methyl group, methoxy group, or a chlorine atom, etc., at 4-position of Ring A, and the substituent on Ring B includes, for example, methyl group, methoxy group and chlorine atom, etc., at 8-position of Ring B.

The enzyme which can be used in the above reduction includes a reductase having ability to asymmetrically reduce the 3-carbonyl group of the compound (II) and converting the compound (II) into the compound (I). Besides, among two optically active cis-compounds (I), i.e., optically active (2S,3S)- and (2R,2R)-compounds, one of these isomers can be preferentially obtained by selecting the enzymes to be used. The origin of reductase includes, for example, a culture, a treated culture of a microorganism having ability to produce such a reductase or a co-enzyme thereof. The culture or treated culture of a microorganism can be used by contacting it with the aggregate of the compound (II).

Suitable examples of the microorganisms having such ability are, yeasts, bacteria, molds, actinomycetes, etc. For example, in order to preferentially obtain optically active (2S,3S)-compounds, the microorganism to be used includes, for example, yeasts belonging to the genus Candida, the genus Debaryomyces, the genus Nematospora, the genus Pichia, the genus Ogataea, the genus Rhodosporidium, the genus Kuraishia, the genus Yamadazyma and the genus Saccharomyces, bacteria belonging to the genus Arthrobacter, the genus Bacillus, the genus Brevibacterium, the genus Corynebacterium and the genus Pseudomonas, actinomycetes belonging to the genus Mycobacterium, the genus Nocardia, the genus Streptomyces, and molds belonging to the genus Penicillium. In order to preferentially obtain optically active (2R,3R)-compounds, the microorganism to be used includes, for example, microorganisms belonging to the genus Rhizopus.

Examples of the above-mentioned microorganisms include *Candida melinii* IFO 0747, *Candida saitoana* IFO 0380, *Candida tropicalis* IFO 0589, *Debaryomyces polymorphus* IFO 1166, *Pichia anomala* IFO 0135, *Kuraishia capsulata* IFO 0721, *Ogataea polymorpha* IFO 1024, *Nematospora coryli* IFO 0658, *Yamadazyma farinosa* IFO 0193, *Yamadazyma halophila* IFO 0947, *Pichia membranaefaciens* IFO 0128, *Ogataea pini* IFO 1793, *Pichia trehalophila* IFO 1683, *Rhodosporidium toruloides* IFO 1638, *Saccharomyces cerevisiae* IFO 1346, *Saccharomyces cerevisiae* IFO 2345, *Saccharomyces cerevisiae* (baker's yeast produced by Oriental Yeast Co., Ltd.), *Arthrobacter paraffineus* ATCC 15591, *Bacillus pumilus* IFO 12087, *Bacillus substilis* IFO 3026, *Corynebacterium glutamicum* ATCC 14067, *Brevibacterium ketoglutamicum* ATCC 15588, *Pseudomonas putida* ATCC 17484, *Mycobacterium smegmatis* ATCC 607, *Nocardia asteroides* IFO 3384, Ditto IFO 3423, *Streptomyces lavendulae* IFO 3145, *Streptomyces rimosus* IFO 3441, *Penicillium chrysogenum* IFO 4626, *Rhizopus oryzae* IFO 4758, Ditto IFO 5780, and the like.

The microorganism to be used in the present invention may be any microorganism having ability to convert the compound (II) into the optically active compound (I) by asymmetrical reduction. The microorganism may be a strain which is newly separated from soil, food, an animal or the like. Moreover, there may be a mutant strain obtained by artificial treatment such as irradiation of UV ray or treatment with a mutating agent or a strain derived from the above microorganism by a genetic engineering or bioengineering means such as gene recombination or cell fusion.

The culture or treated culture of the microorganism in the present invention is any culture or treated culture so long as it has ability to convert the compound (II) into the optically active compound (I) by asymmetric reduction. Examples of the culture include a culture broth or living cells. Examples of the treated culture include a treated culture broth such as a culture supernatant, treated cells such as washed cells, dried cells, ground cells, an autolysate of cells, an extract of cells, or a partially purified or purified enzyme obtained therefrom according to the conventional manner (e.g., fractionation with ammonium sulfate, ion-exchange chromatography, gel-filtration chromatography or the like).

The culture (culture broth or the living cells) of the above-mentioned microorganism can be obtained by culturing the microorganism in a conventional culture medium, for example, in a medium containing conventional carbon sources, nitrogen sources and inorganic salts, at room temperature or under warming (preferably, at a temperature from about 20 to 40° C.) under aerobic conditions, at pH 2 to pH 8, and then if necessary, by separating and collecting the cells from the culture broth by a conventional method.

The culture or the treated culture of the microorganism may be immobilized by known methods such as the methods using polyacrylamide, a sulfur-containing polysaccharide gel (e.g. carrageenan gel), an alginic acid gel or an agar gel, etc., before use.

The asymmetric reduction of the present invention can be carried out by permitting the culture or the treated culture of the microorganism to contact with the aggregate of 2-phenyl-1,5-benzothiazepin-3,4(2H,5H)-dione compound (II) and incubating the mixture.

The concentration of the substrate: the aggregate of the compound (II) may be generally in the range of about 0.5 to 80% (w/v), preferably 2 to 30% (w/v), and the reaction can be carried out at room temperature or under heating, preferably at a temperature from 10 to 50° C., more preferably at a temperature from 25 to 40° C. During the reaction, it is preferable to adjust the pH value of the reaction mixture to 2 to 10, more preferably 5 to 8. As the aggregate of the compound (II) used as a substrate shows an improved solubility in water, it is not necessary to supplementarily use a solubilizer, but if necessary, it is possible to use a small amount of dimethylformamide, dimethyl sulfoxide, or a lower alcohol (e.g., methanol, ethanol). Besides, the substrate may be added at once at the beginning of the reaction, or may be added in several portions during the reaction. Water is the most preferable reaction solvent, but the reaction can be carried out in a two-phase solvent system of an aqueous solvent (e.g., water, etc.) and an organic solvent (e.g., benzene, n-hexane, diethyl ether, diisopropyl ether, toluene, ethyl acetate, etc.).

After the reaction is completed, the desired optically active 3-hydroxy-2-phenyl-2,3-dihydro-1,5-benzothiazepin-4(5H)-one compound (I) can be obtained by extracting the reaction mixture with an organic solvent such as toluene, chloroform, ethyl acetate, acetone, etc., and treating the extract with a conventional method such as concentration, chromatography, distillation, etc.

The starting compound (II) of the present invention may be prepared by the method disclosed in JP-A-60-25982 or JP-A-60-25983.

That is, the starting compound (II) is prepared by oxidizing cis-3-hydroxy-2-phenyl-2,3-dihydro-1,5-benzothiazepin-4(5H)-one compound which is disclosed in JP-B-45-9383 with using a mixture of dimethylsulfoxide and acetic anhydride and hydrolyzing the resultant product with conc. aqueous ammonia or an aqueous sodium hydroxide solution.

Moreover, the optically active compound (I) obtained in the above-mentioned process can be converted into an optically active 1,5-benzothiazepine derivative of the formula (III):

(III)

wherein $R^1$ is a lower alkanoyl group or a lower alkoxycarbonyl-lower alkyl group, $R^2$ is a lower alkyl group, $R^3$ is a lower alkyl group or a lower alkoxy-phenyl-lower alkyl group, Y is a lower alkylene group, and Ring A and Ring B are the same as defined above, by a known method, and if necessary, further converting the compound (III) into a pharmaceutically acceptable salt thereof.

For example, the compound (III) is prepared by condensing the compound (I) with a compound of the formula (IV):

$R^1OH$ (IV)

wherein $R^1$ is the same as defined above, or a reactive derivative thereof, converting the resulting optically active 1,5-benzothiazepine derivative of the formula (V):

(V)

wherein $R^1$, Ring A and Ring B are the same as defined above, to an alkali metal salt thereof at the 5-nitrogen atom of the benzothiazepine nucleus, and condensing the alkali metal salt with a compound of the formula (VI):

(VI)

wherein X is a halogen atom, and $R^2$, $R^3$ and Y are the same as defined above.

In the group: —Y—N($R^2$)($R^3$) which is positioned at the 5-position of the benzothiazepine nucleus of the compound (III), Y is preferably ethylene group, $R^2$ is preferably methyl group, and $R^3$ is preferably methyl group or methoxy-phenylethyl group.

In the above process, the condensation reaction with the compound (IV) and the condensation reaction with the compound (VI) can be carried out vise verse. That is, the alkali metal salt of the compound (I) is firstly condensed with the compound (VI), and then the resultant is condensed with the compound (IV).

Throughout the present claims and specification, the lower alkyl group, the lower alkoxy group and the lower alkylene group mean ones having 1 to 6 carbon atoms. The lower alkanoyl group means ones having 2 to 7 carbon atoms. The halogen atom is chlorine atom, bromine atom, fluorine atom or iodine atom.

EXAMPLES

The present invention will be illustrated in detail by the following Examples, but should not be construed to be limited thereto.

Examples 1–4

The crystals of 2-(4-methoxyphenyl)-1,5-benzothiazepin-3,4(2H,5H)-dione (compound (II)) (1.5 g) is dissolved in various polar organic solvents as listed in Table 1, and the solution thus obtained is added to water (150 ml), and the mixture is stirred at room temperature for one hour. The mixture is centrifuged, and the resulting precipitates are washed and dried to quantatively give a powdery aggregate of 2-(4-methoxyphenyl)-1,5-benzothiazepin-3,4(2H,5H)-dione.

The physicochemical properties of the powdery aggregate of the compound (II) prepared by using a primary solvent and water as a secondary solvent and its solubility in water at 30° C. are shown in Table 1.

TABLE 1

| | | Powdery aggregate of the compound (II) | |
|---|---|---|---|
| Ex. No. | Primary solvent | Physicochemical properties | Solubility in water at 30° C. |
| 1 | DMF (9 ml) | M.p. 130–140° C. Pale yellow powder | 20–23 mg/l |
| 2 | DMF (9 ml) | M.p. 130–140° C. Pale yellow powder | 20–23 mg/l |
| 3 | DMSO (15 ml) | M.p. 120–125° C. Pale yellow powder | 22–25 mg/l |
| 4 | Methanol (110 ml) | M.p. 130–135° C. Pale yellow powder | 22–24 mg/l |

Figure 2:
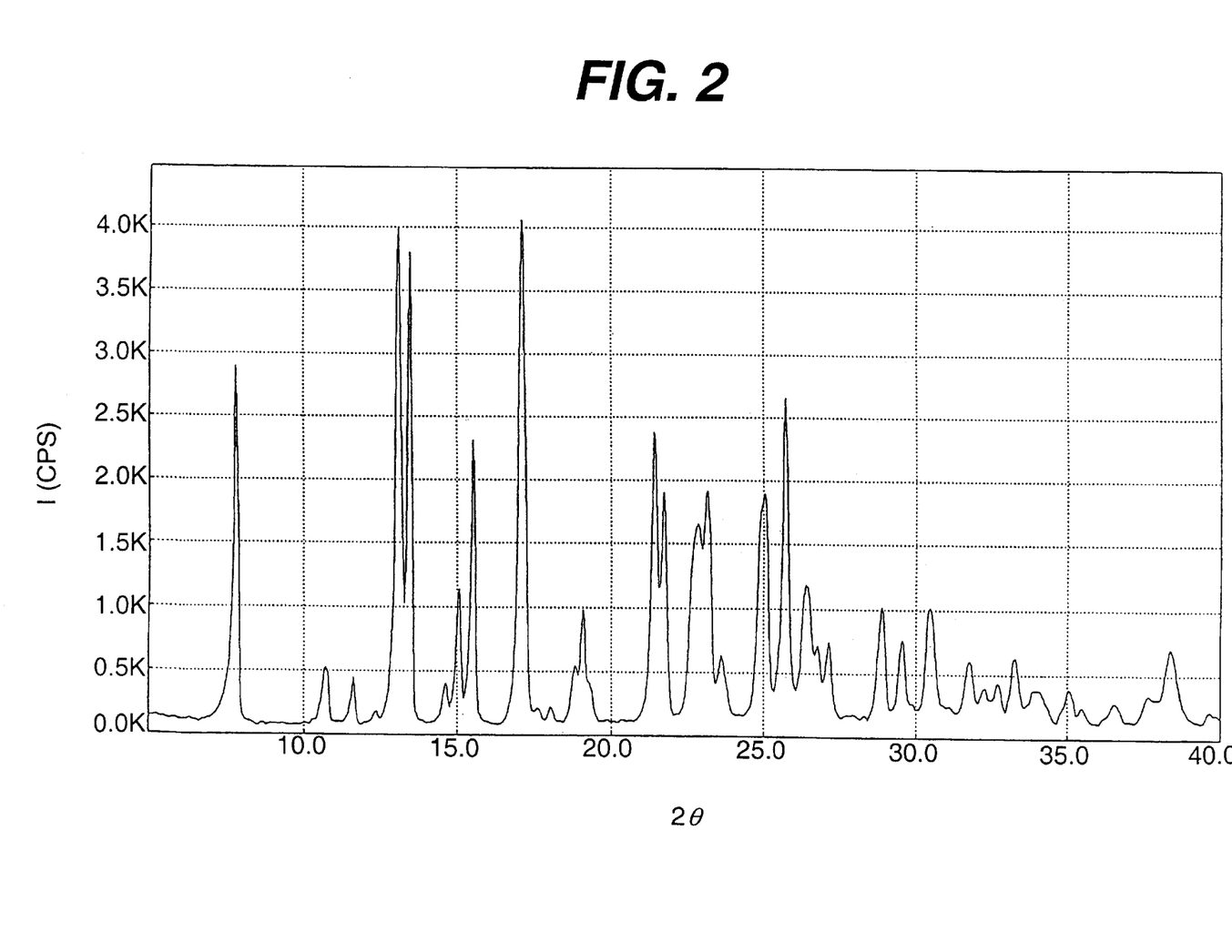
FIG. 2 shows the X-ray powder diffraction pattern of the crystals of 2-(4-methoxyphenyl)-1,5-benzothiazepin-3,4 (2H,5H)-dione.

The X-ray powder diffraction patterns of the powdery aggregate of the compound (II) obtained in Examples 1 to 4 are shown in FIG. 1. As is shown in FIG. 1, all of the aggregates of the compound (II) shows specific diffraction peaks around at angles: $2\theta=8.0$, 9.9 and 15.1, which are quite different from the X-ray diffraction pattern of the crystals of the compound (II) as shown in FIG. 2.

Meanwhile, the X-ray diffraction analysis was carried out under the following condition.

X-ray generator: 3 kW

X-ray source: Cu, 1.54050 Å

Voltage and Amperage of X-ray tube: 40 kV, 35 mA

Recording breadth: 0.02°

Scanning speed: 4.0°/min.

Emission slit: 1.00°

Scattering slit: 1.00°

Receiving slit: 0.15 mm

Besides, the d value (Interplanner Spacing; Å) and the relative X-ray intensity of each aggregate of Examples 1, 2 3 and 4 obtained by the above-mentioned X-ray powder diffractometry are shown in Tables 2, 3, 4 and 5.

TABLE 2

(aggregate of Example 1)

| 2θ | d value | Relative Intensity |
|---|---|---|
| 8.0200 | 11.0145 | 407 |
| 9.8400 | 8.9807 | 793 |
| 13.1600 | 6.7218 | 70 |
| 15.0200 | 5.8935 | 1000 |
| 17.7400 | 4.9953 | 206 |
| 18.0400 | 4.9131 | 114 |
| 21.7400 | 4.0845 | 137 |
| 22.1800 | 4.0044 | 238 |
| 23.0400 | 3.8569 | 69 |
| 24.8400 | 3.5813 | 77 |
| 27.6000 | 3.2292 | 58 |
| 37.7800 | 2.3792 | 37 |

TABLE 3

(aggregate of Example 2)

| 2θ | d value | Relative Intensity |
|---|---|---|
| 8.0200 | 11.0145 | 393 |
| 9.8800 | 8.9446 | 823 |
| 13.2000 | 6.7016 | 66 |
| 15.0600 | 5.8779 | 1000 |
| 17.7600 | 4.9898 | 211 |
| 18.1400 | 4.8862 | 96 |
| 21.4600 | 4.1371 | 78 |
| 21.6400 | 4.1031 | 132 |
| 22.0000 | 4.0369 | 177 |
| 22.3400 | 3.9762 | 245 |
| 22.5800 | 3.9344 | 139 |
| 24.8600 | 3.5785 | 72 |
| 26.6400 | 3.3433 | 76 |
| 27.5800 | 3.2315 | 61 |

TABLE 4

(aggregate of Example 3)

| 2θ | d value | Relative Intensity |
|---|---|---|
| 8.0400 | 10.9866 | 373 |
| 9.8800 | 8.9446 | 801 |
| 13.2200 | 6.6913 | 65 |
| 15.0600 | 5.8779 | 1000 |
| 17.7800 | 4.9844 | 199 |
| 18.1200 | 4.8915 | 100 |
| 21.5000 | 4.1296 | 77 |
| 21.8000 | 4.0734 | 135 |
| 22.3200 | 3.9797 | 245 |
| 23.1600 | 3.8372 | 71 |
| 24.8200 | 3.5842 | 64 |
| 27.8000 | 3.2064 | 61 |
| 29.8400 | 2.9916 | 40 |
| 30.5800 | 2.9209 | 41 |
| 37.7000 | 2.3841 | 30 |

TABLE 5

(aggregate of Example 4)

| 2θ | d value | Relative Intensity |
|---|---|---|
| 8.0800 | 10.9326 | 477 |
| 9.9200 | 8.9087 | 926 |
| 13.2600 | 6.6712 | 64 |
| 15.2400 | 5.8089 | 1000 |
| 17.9600 | 4.9347 | 196 |
| 18.3200 | 4.8384 | 73 |
| 21.2400 | 4.1794 | 27 |
| 21.4400 | 4.1410 | 31 |
| 22.3200 | 3.9797 | 127 |
| 22.5800 | 3.9344 | 128 |
| 23.3800 | 3.8016 | 52 |
| 24.9000 | 3.5729 | 40 |
| 25.1000 | 3.5448 | 40 |
| 28.0000 | 3.1839 | 41 |
| 28.2200 | 3.1596 | 30 |
| 30.0200 | 2.9741 | 40 |
| 30.8200 | 2.8988 | 40 |
| 31.0800 | 2.8751 | 28 |
| 37.9400 | 2.3695 | 22 |

Example 5

Baker's yeast (11.2 g) was suspended in a mixture of ethanol (0.575 ml) and water (50 ml), and thereto was added 100 mg of the crystals of 2-(4-methoxyphenyl)-1,5-benzothiazepin-3,4(2H,5H)-dione or a powdery aggregate thereof obtained in any one of Examples 1, 3 and 4, and the mixture was incubated with shaking at 80 rpm at 30° C. for 24 hours.

In these reaction mixtures, the conversion rate from the starting compound into (2S,3S)-3-hydroxy-2-(4-methoxyphenyl)-2,3-dihydro-1,5-benzothiazepin-4(5H)-one was periodically determined. The results are shown in FIG. 3.

Figure 3:
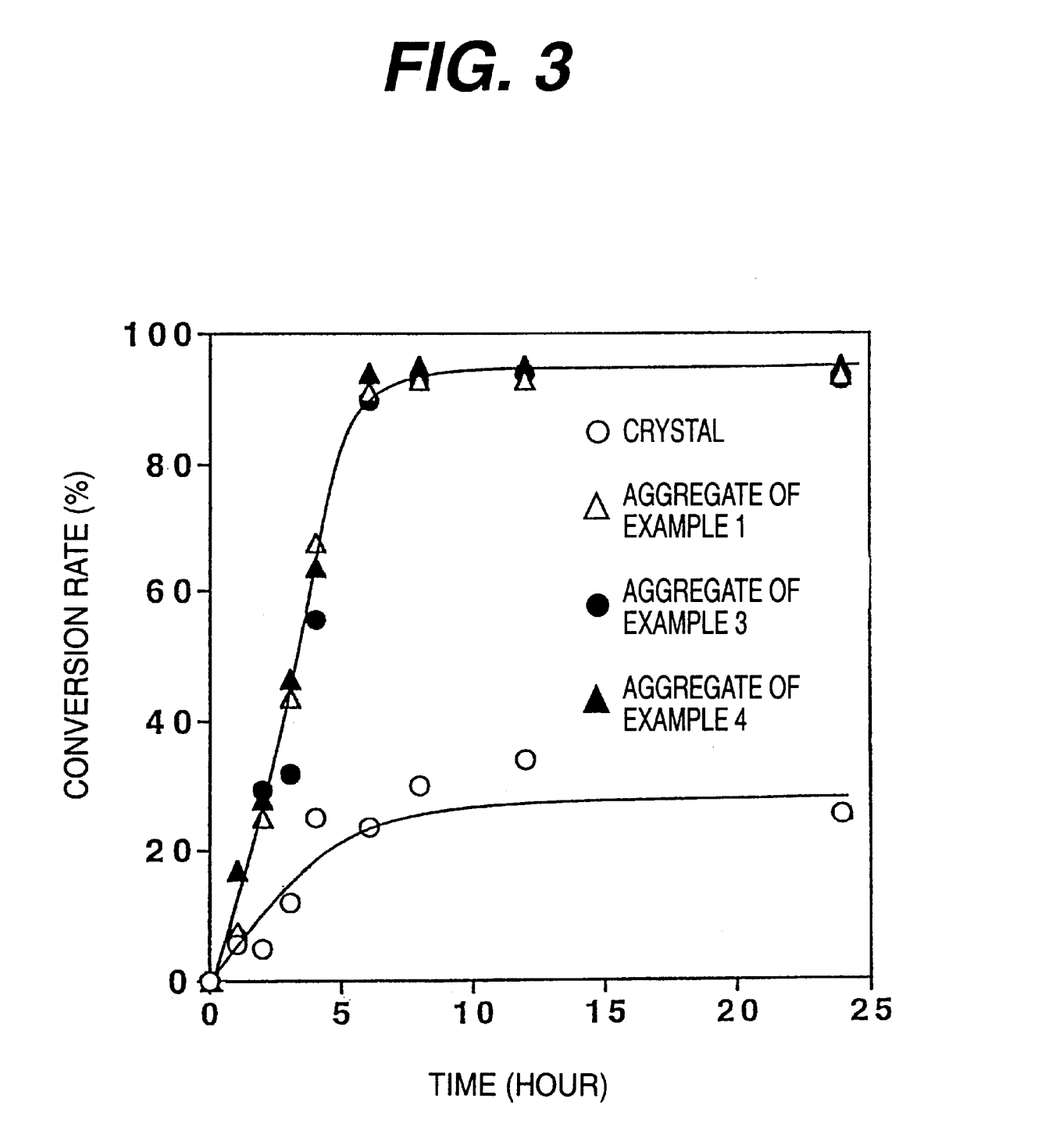
FIG. 3 is a graph showing the conversion rates from the crystals of 2-(4-methoxyphenyl)-1,5-benzothiazepin-3,4 (2H,5H)-dione or the aggregates obtained in Examples 1, 3 and 4, into (2S,3S)-3-hydroxy-2-(4-methoxyphenyl)-2,3-dihydro-1,5-benzothiazepin-4(5H)-one, by enzymatic reduction using baker's yeast.

As is shown in FIG. 3, when the powdery aggregate of the present invention was used as a starting compound, the conversion rate from the compound (II) into the desired optically active compound was more than 90% in a rather short time (about five hours), but when the crystals of the compound (II) was used, the conversion rate from the compound (II) into the desired optically active compound was low, i.e., still 20% or so even 24 hours later.

Example 6

(1) Preparation of aggregate:

2-(4-Methoxyphenyl)-1,5-benzothiazepin-3,4(2H,5H)-dione (4 g) was dissolved in DMF (24 ml), and the solution thus obtained was added dropwise under moderately stirring into water (400 ml) over a period of five minutes at room temperature. The mixture was stirred at room temperature for one hour, and then centrifuged at 3000 rpm for three minutes. The powdery material thus collected was washed twice with water to quantatively give a powdery aggregate.

(2) Reduction reaction:

The above aggregate (4 g, after drying in the air) was suspended in water (50 ml) in a 300 ml Erlenmeyer flask, and thereto were added compressed baker's yeast (11.2 g) and ethanol (0.75 ml) (200 mM), and the mixture was aerobically shaken at 80 rpm at 30° C. Then, the same amount of ethanol was added at intervals of 12 hours for 9 days, and the reduction reaction was carried out.

To the reaction mixture was added acetone (300 ml), and the mixture was stirred for one hour, and filtered. The filtrate was concentrated, and allowed to stand in a refrigerator at 4°

C. for four hours. The mixture was filtered with suction, and dried in the air to give crude crystals of (2S,3S)-3-hydroxy-2-(4-methoxyphenyl)-2,3-dihydro-1,5-benzothiazepin-4(5H)-one (3.9 g). The crude crystals were further recrystallized from methanol to give crystals having a purity of more than 99% in an yield of 82.5%.

Figure 4:
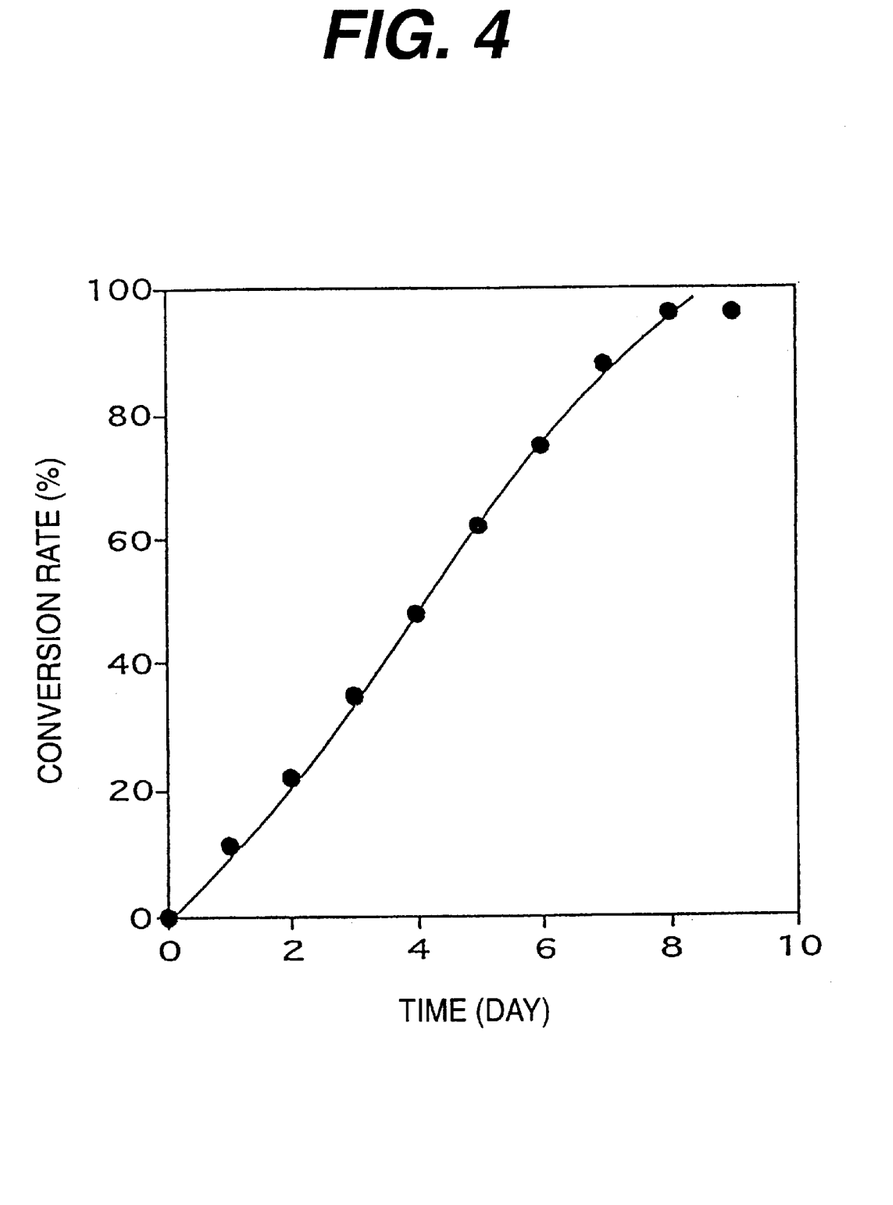
FIG. 4 is a graph showing the conversion rate of the powdery aggregate by enzymatic reduction in Example 6.

In the above reaction, the conversion rate into the desired compound was determined every day. The results are shown in FIG. 4.

Example 7

The wet aggregate (5 g, after drying in the air) obtained in the same manner as in Example 6-(1) was suspended in water (50 ml) in a 500 ml shaking flask, and thereto were added compressed baker's yeast (16.8 g) and glucose (1.8 g) (200 mM). The mixture was aerobically shaken at 80 rpm at 30° C. for 9 days for reduction, during which the same amount of glucose was added to the mixture at every 24 hours.

To the reaction mixture was added acetone (300 ml), and the mixture was stirred for one hour, and filtered. The filtrate was concentrated, and the precipitated crystals were collected by filtration with suction, and dried in the air to give crude crystals of (2S,3S)-3-hydroxy-2-(4-methoxyphenyl)-2,3-dihydro-1,5-benzothiazepin-4(5H)-one (4.5 g). The crude crystals were further recrystallized from methanol to give crystals having a chemical purity of more than 99%, an optical purity of more than 99%, and m.p. 208–210° C., in an yield of 80%.

Figure 5:
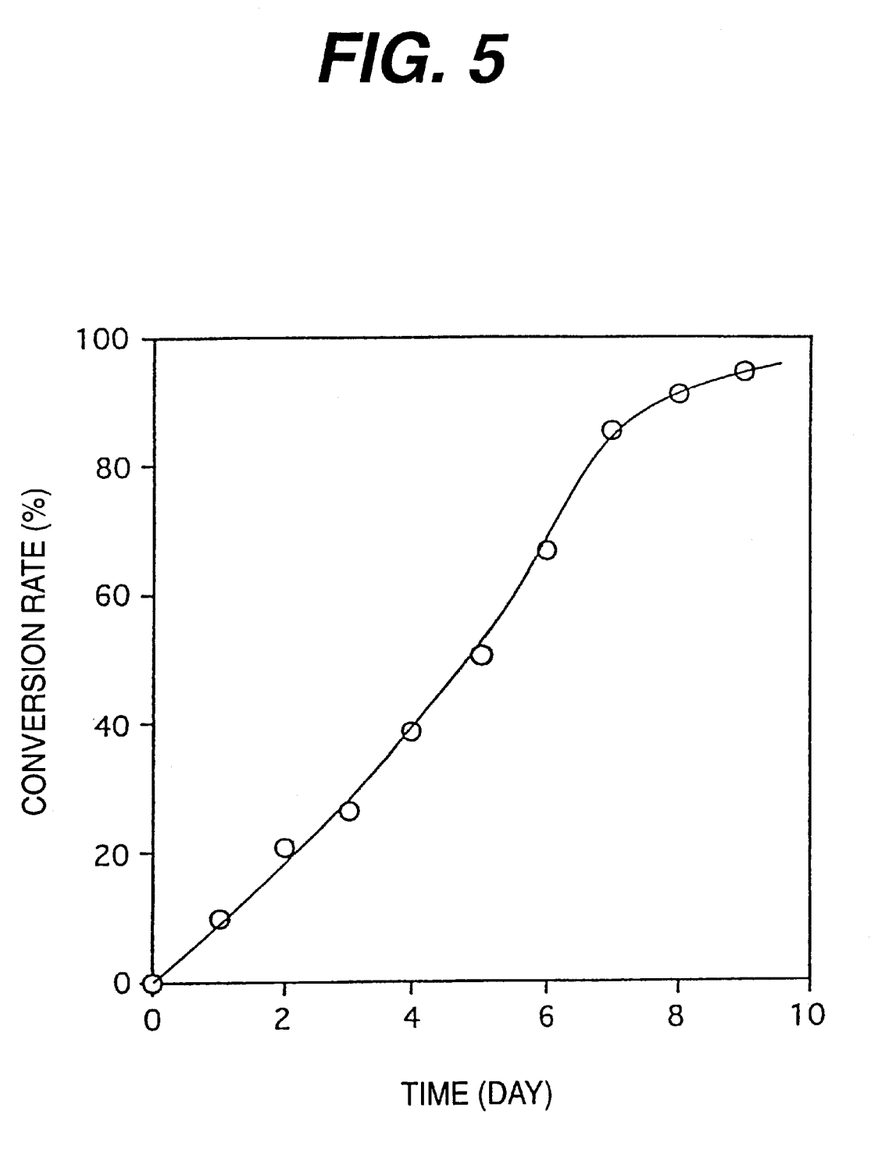
FIG. 5 is a graph showing the conversion rate of the powdery aggregate by enzymatic reduction in Example 7.

In the above reaction, the conversion rate into the desired compound was determined every day. The results are shown in FIG. 5.

EFFECTS OF INVENTION

According to the present invention, the desired optically active 3-hydroxy-2-phenyl-2,3-dihydro-1,5-benzothiazepin-4(5H)-one compounds can be produced with high efficiency on an industrial scale by subjecting a powdery aggregate of the starting 2-phenyl-1,5-benzothiazepin-3,4(2H,5H)-dione compound having an improved solubility in water, wherein the large amount of the starting compounds can be used without using a solubilizer.

What is claimed is:

1. A powdery aggregate of a 2-phenyl-1,5-benzothiazepin-3,4(2H,5H)-dione compound of the formula (II):

(II)

wherein Ring A and Ring B are each a benzene ring which may optionally be substituted by a group selected from the group consisting of a lower alkyl group, a lower alkoxy group and a halogen atom, said powdery aggregate being prepared by dissolving crystals of said compound of formula (II) in a polar organic solvent to form a solution, admixing the solution with water to form particles of said compound, and then separating and collecting the resultant particles to provide a powdery aggregate of the compound of formula (II).

2. The powdery aggregate according to claim 1, which has a melting point in the range of 120° C. to 140° C.

3. The powdery aggregate according to claim 1, wherein the aggregate has an X-ray powder diffraction pattern ($\lambda$=1.54050 Å) as follows:

a) a single and clear diffraction peak is at around $2\theta$=8.0°m $2\theta$=9.9° and $2\theta$=15.1°, respectively, b) a diffraction peak at around $2\theta$=15.1° has a maximum relative X-ray intensity among all peaks, and c) when the relative intensity of the peak at around $2\theta$=15.1° is adjusted to 1.00, the relative intensity of the peaks at around $2\theta$=8.0° and $2\theta$=9.9° is in the range of about 0.30 to 0.50 and about 0.70 to 0.95, respectively and no peak other than those mentioned above has a relative X-ray intensity of more than 0.30.

4. The powdery aggregate according to any one of claims 1, 2, and 3, wherein the compound of formula (II) is 2-(4-methoxyphenyl)-1,5-benzothiazepin-3,4(2H,5H)-dione.

5. The powdery aggregate according to claim 4, which shows a solubility of more than 20 mg/liter in water at 30° C.

6. The powdery aggregate according to claim 1, wherein the polar organic solvent is a polar organic solvent which can dissolve the compound of formula (II) at a concentration of more than 1 mg/ml at 30° C., and has a dielectric constant of more than 25.

7. The powdery aggregate according to claim 6, wherein the polar organic solvent is dimethyl sulfoxide, N,N-dimethylformamide or methanol.

8. A powdery aggregate of the compound having a melting point in the range of 120° C. to 140° C.; and having an X-ray powder diffraction pattern ($\lambda$=1.54050 Å) as follows:

a) a single and clear diffraction peak is at around $2\theta$=8.0°, $2\theta$=9.9° and $2\theta$=15.1°, respectively, b) a diffraction peak at around $2\theta$=15.1° has a maximum relative X-ray intensity among all peaks, and c) when the relative intensity of the peak at around $2\theta$=15.1° is adjusted to 1.00, the relative intensity of the peaks at around $2\theta$=8.0° and $2\theta$=9.9° is in the range of about 0.30 to 0.50 and about 0.70 to 0.95, respectively and no peak other than those mentioned above has a relative X-ray intensity of more than 0.30.

9. The powdery aggregate of claim 1, which comprises a mixture of a crystalline form and an amorphous form of the compound of formula (II).

* * * * *

UNITED STATES PATENT AND TRADEMARK OFFICE
CERTIFICATE OF CORRECTION

PATENT NO. : 5,945,533
DATED : August 31, 1999
INVENTOR(S) : Tadashi KOMETANI et al.

It is certified that error appears in the above-identified patent and that said Letters Patent is hereby corrected as shown below:

In Claim 3, column 12, line 12, "$2\theta=8.0°m$" should read --$2\theta=8.0°$,--.

Signed and Sealed this

Twentieth Day of June, 2000

Attest:

Q. TODD DICKINSON

*Attesting Officer*  *Director of Patents and Trademarks*